United States Patent [19]
Lebl et al.

[11] Patent Number: 5,338,831
[45] Date of Patent: * Aug. 16, 1994

[54] METHOD OF MAKING MULTIPLE SYNTHESIS OF PEPTIDES ON SOLID SUPPORT

[75] Inventors: Michal Lebl, Praha, Czechoslovakia; Jutta Eichler, Berlin, Fed. Rep. of Germany; Vit Pokorny, Praha, Czechoslovakia; Jiři Jehnička, Praha, Czechoslovakia; Petr Mudra, Praha, Czechoslovakia; Karel Ženíšek, Praha, Czechoslovakia; Alena Stierandová, Červený Kostelec, Czechoslovakia; Jan Kalousek, Praha, Czechoslovakia; Jan Bolf, Praha, Czechoslovakia

[73] Assignee: Academy of Sciences of the Czech Republic changed from Ceskoslovenska akademie ved, Praha, Czechoslovakia

[ * ] Notice: The portion of the term of this patent subsequent to Apr. 13, 2010 has been disclaimed.

[21] Appl. No.: 992,288

[22] Filed: Dec. 14, 1992

Related U.S. Application Data

[63] Continuation of Ser. No. 645,121, Jan. 24, 1991, Pat. No. 5,202,418.

[30] Foreign Application Priority Data

Feb. 2, 1990 [CS] Czechoslovakia ............... PV 508-90

[51] Int. Cl.$^5$ ............................................. A61K 37/02
[52] U.S. Cl. ............................. 530/334; 530/333; 422/64; 422/72; 422/116
[58] Field of Search ............... 530/333, 334, 811, 812, 530/815, 817; 422/64, 72, 116; 435/299, 300, 301; 935/88

[56] References Cited

U.S. PATENT DOCUMENTS

| | | | |
|---|---|---|---|
| 3,531,258 | 11/1967 | Merrifield et al. | 23/252 |
| 3,557,077 | 9/1967 | Brunfeldt et al. | 260/112.5 |
| 3,647,390 | 3/1972 | Kubodera et al. | 422/129 |
| 3,715,190 | 9/1973 | Won Kil Park et al. | 23/252 R |
| 4,325,910 | 4/1982 | Jordan | 422/64 |
| 4,412,973 | 11/1983 | Guigan | 422/72 |
| 4,631,211 | 12/1986 | Houghten | 428/35 |
| 4,668,476 | 5/1987 | Bridgham et al. | 422/62 |
| 4,680,164 | 7/1987 | Kelln | 422/72 |
| 4,746,490 | 5/1988 | Saneii | 422/116 |
| 4,748,002 | 5/1988 | Neimark et al. | 422/116 |
| 5,010,175 | 4/1991 | Rutter et al. | 530/334 |
| 5,202,418 | 4/1993 | Lebl et al. | 422/72 |

FOREIGN PATENT DOCUMENTS

| | | |
|---|---|---|
| 0196174 | 3/1986 | European Pat. Off. . |
| 385433 | 9/1990 | European Pat. Off. . |
| 2194176 | 3/1988 | United Kingdom . |

OTHER PUBLICATIONS

Eichler, "Application of Cellulose Paper as Support Material in Simultaneous Solid Phase Synthesis," Collect. Czech. Chem. Commun., vol. 54, pp. 1746–1752 (1989).

Merrifield, *Angewandte Chemie* vol. 24, No. 10 (Oct. 1985) at 799–810.

Houghten, *PRNS USA* vol. 82 5131–5135 (Aug. 1985).

Frank et al., *Tetrahedron* vol. 44, No. 19 6031–6040 (1988).

*Primary Examiner*—James C. Housel
*Assistant Examiner*—Lien Tran
*Attorney, Agent, or Firm*—Dressler, Goldsmith, Shore & Milnamow, Ltd.

[57] ABSTRACT

A method is disclosed for performing a multiple synthesis of peptides on a solid carrier. Active components are successively bonded to functional groups anchored on a carrier. The carrier is a planar porous material divided into functionalized compartments, into which an active component is put, via a dispensing head.

6 Claims, 3 Drawing Sheets

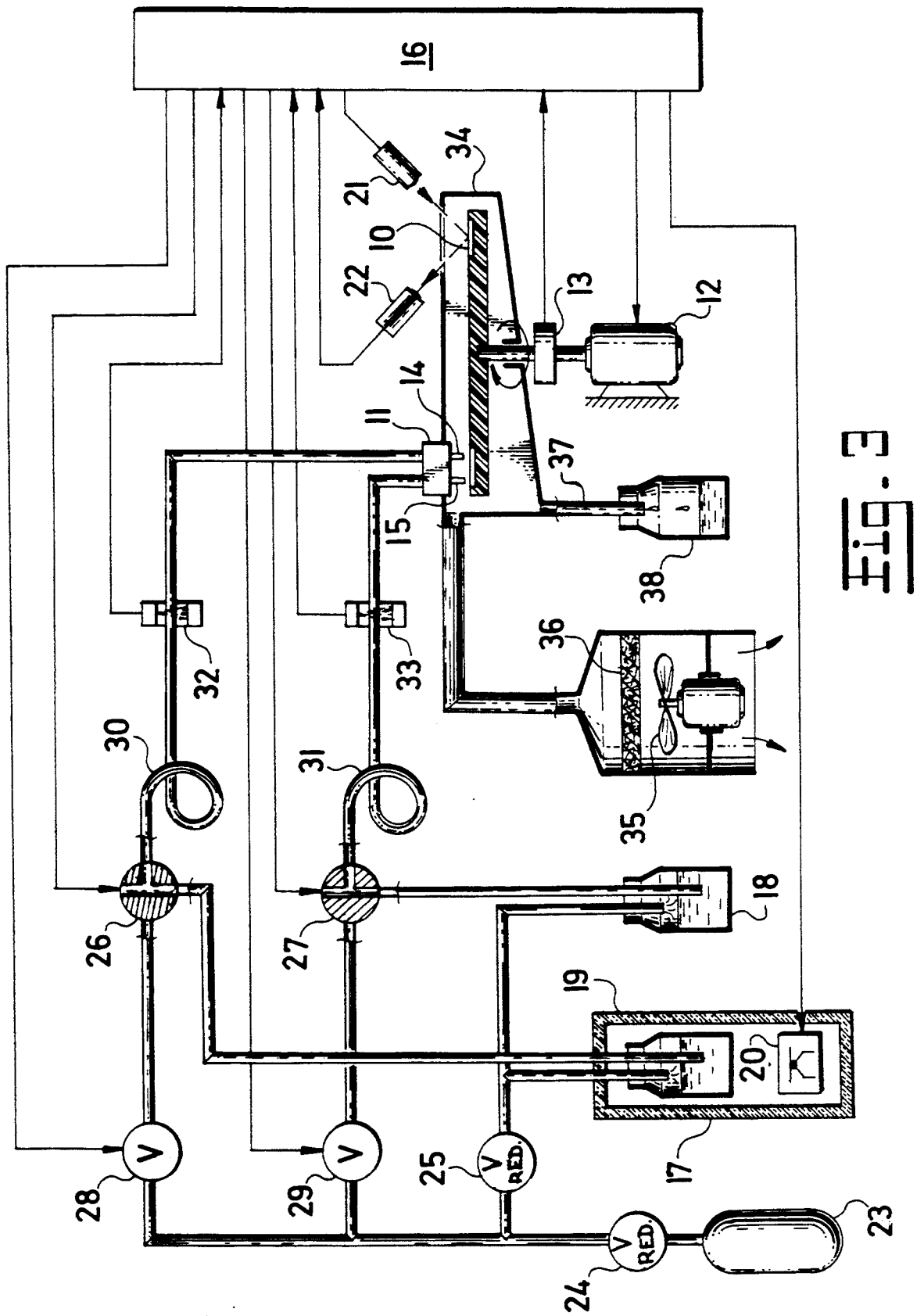

METHOD OF MAKING MULTIPLE SYNTHESIS OF PEPTIDES ON SOLID SUPPORT

CROSS-REFERENCE TO RELATED APPLICATION

This application is a continuation of U.S. patent application Ser. No. 07/645,121 filed Jan. 24, 1991, now U.S. Pat. No. 5,202,418.

TECHNICAL FIELD OF THE INVENTION

This invention relates to a method for carrying out a synthesis of multiple peptides on a solid carrier.

BACKGROUND OF THE INVENTION

Technology for synthesis of peptides has been developed from classical methods applied for synthesis carried out in a solution (a survey of this technology is found in Houben-Weyl, Methoden der Organischen Chemie, Synthese yon Peptiden, E. Wunsch ed., Thieme, Berlin (1974)) through the synthesis technique developed by Merrifield applying a solid carrier in the form of particles (see, e.g., Stewart, J. M., and Young, J. D., Solid Phase Peptide Synthesis, Freeman, San Francisco (1985)). This technique has been found suitable for automation. See, e.g., Merrifield, R. B., Stewart, J. M., and Jernberg, N., Apparatus for the Automated Synthesis of Peptides, U.S. Pat. No. 3,531,258; Brunfeldt, K., Roepstorff, P., and Halstrom, J.; Reactions System, U.S. Pat. No. 3,577,077; Kubodera, J., Hara, T.; and Makabe, H., Apparatus for Synthesis of Peptides or the Like Organic Compounds, U.S. Pat. No. 3,647,390; Won Kil Park and Regoli, D., System for the Solid Phase Synthesis, U.S. Pat. No. 3,715,190; Bridgham, J., et al., Automated Peptide Synthesis Apparatus, U.S. Pat. No. 4,668,490. Such techniques are suitable for parallel synthesis of many peptides. See, e.g., Verbander, H. S., Fuller, W. D., and Goodman M., Rapid, Large Scale, Automatable High Pressure Peptide Synthesis, U.S. Pat. No. 4,192,798; Neimark, J., and Brand, J. P., Semi-Automatic, Solid-Phase Peptide Multi-Synthesizer and Process for the Production of Synthetic Peptides by the Use of Multi-Synthesizer and Process for the Production of Synthetic Peptides by the Use of Multi-Synthesizer, U.S. Pat. No. 4,748,002; Houghten, R. A., Means for Sequential Solid-Phase Organic Synthesis and Methods Using the Same, European Patent Application Publication No. 196,174 published Jan. 10, 1986; Geysen, H. M., Meloen, R. H., and Bartcling, S. J., Proc. Natl. Acad. Sci. U.S.A., Vol. 81, Page 3998 (1984); Frank, R., and Doring, R., "Simultaneous Multiple Peptide Synthesis under Continuous Flow Conditions on Cellulose Paper Discs as Segmental Solid Supports," Tetrahedron, Vol. 44, No. 19, page 6031 (1988); Eichler, J., Beyermann, M., and Bienert, M., "Application of Cellulose Paper as Support Material in Simultaneous Solid Phase Peptide Synthesis" Collect. Czech. Chem. Commun., Vol 54, page 1746 (1989); Krchnak, V., Vagner, J., and Mach, O., "Multiple Continuous Flow Solid-Phase Peptide Synthesis," Int. J. Peptide Protein Res., Vol 33, page 209 (1989). The application of planar continuous carriers made it possible to carry out the so-called continuous synthesis of peptides. See Lebl M., Gut, V., Eichler, J., Krchnak, V. Vagner, J., and Stepanek, J., Method of a Continuous Peptide Synthesis on a Solid Carrier, Czechoslovak Patent Application No. PV 1280-89, to which European Patent Application Publication No. 385,433 published Sep. 5, 1990, corresponds.

The present development of molecular biology requires the preparation of many peptides and their anchoring onto various carriers which enable their application in many immunological tests. Hitherto described methods for the multiple synthesis of peptides are not suitable for automation (Houghten R. A., Means for Sequential Solid Phase Organic Synthesis and Methods Using the Same, European Patent Application Publication No. 196,174, supra), or they give only a limited quantity of yield, the quality of which cannot be verified in an analytical way (Geysen H. M., Meloen R. H. and Bartcling S. J., Proc. Natl. Acad. Sci. U.S.A. 81, 3998, 1984). Devices applying a carrier in the form of particles exhibit the drawback residing in the necessity to split off the peptide and its new anchoring for later applications. Another drawback of hitherto methods resides in a high consumption of solvents during the synthesis.

SUMMARY OF THE INVENTION

The above mentioned drawbacks are obviated by the method for carrying out a multiple synthesis of peptides on a solid carrier with a successive connection of active components onto functional groups anchored on a planar, functionalized, porous carrier and by the apparatus for performing this method according to the invention. The principle of the method resides in that individual activated components are put into separated carriers, while common synthesis steps of corresponding components of various peptides proceed in all compartments of the carrier at the same time. According to the described method, all liquids and solutions of agents are sucked into the carrier and their removal is carried out by pressing the carrier with a dry porous material or by centrifuging the carrier. The apparatus is formed by a planar carrier which is divided into individual compartments and by a frame situated parallel to the carrier and comprising windows filled with inert porous material, the position of which on the frame corresponds with the position of compartments on the planar carrier, and positions of the carrier and frame are mutually adjustable. Another variant of the apparatus consists of a planar carrier divided into individual compartments situated along the circumference of a revolvingly seated disk provided with means for connecting a driving device. Over the disk, at the spot into which individual compartments enter, a dosing head is situated. Over the disk level there is situated a source and detector of a light radiation for monitoring the course of condensation reactions of activated components.

An advantage of the invention resides in an automatic parallel performing of condensation reactions causing an increase of a peptidic chain in individual compartments comprising a planar carrier and in simultaneous washing steps and steps resulting in removing temporary protective groups in all compartments with the planar carrier. An important advantage resides in monitoring the course of the chemical reaction and its computer evaluation, by which the synthesis is considerably shortened and made more effective. Another advantage resides in a considerable decrease of solvent consumption during the synthesis and in the possibility to utilize the peptide bonded on the carrier for further applications.

BRIEF DESCRIPTION OF THE DRAWINGS

FIG. 3 is a block diagram showing the operation of the apparatus of FIG. 2 in a method according to the present invention.

DETAILED DESCRIPTION OF ILLUSTRATED EMBODIMENTS

Figure 1:
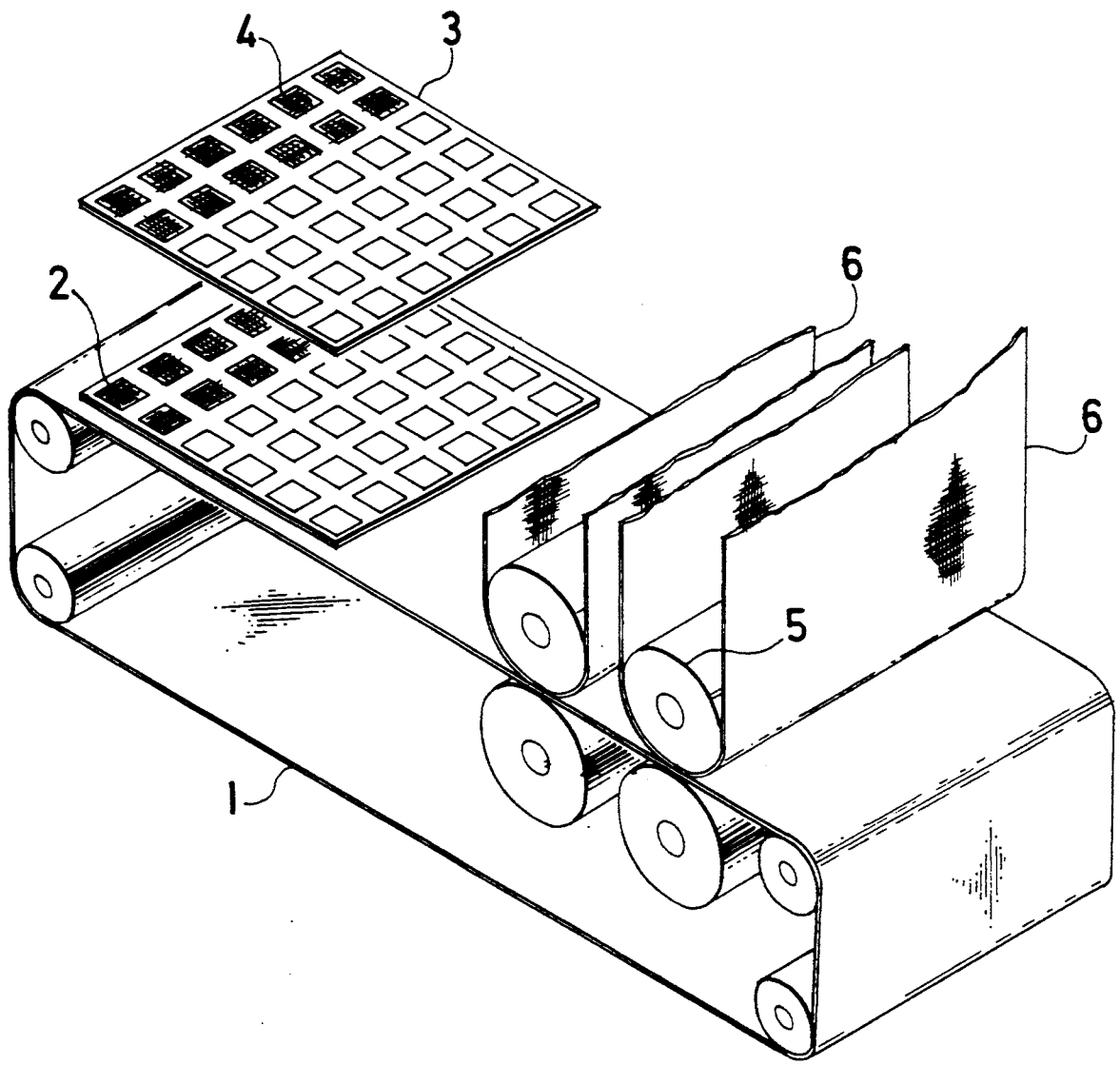
FIG. 1 is an enlarged schematic perspective view of an apparatus with a linear shift capacity for performing a multiple synthesis of peptides on a planar carrier.

The apparatus according to FIG. 1 is formed by a band 1 made of inert material e.g. polyamide or polypropylene, on which there is situated a planar carrier divided in compartments 2. A frame 3 comprising windows 4 filled with inert material which is able to carry by means of capillary forces, an agent solution of pure solvent, is situated in such a way that these windows 4 may correspond with the defined compartments 2 of the planar carrier. The apparatus is also provided with hold-down rollers 5, situated one opposite the other, on which a porous dry foil 6 is seated.

By pressing down the frame 3 to the carrier, a transfer of liquid from windows 4 to compartments 2 takes place. The material of the individual compartments 2 has a higher affinity for the transferred liquid and that is why the major part of the solution is transferred. Glass fiber and other cotton are a suitable combination of materials for windows 4 and compartments 2 respectively. In this case 80% of the liquid is transferred from the window 4 into the compartment 2 where the liquid is dimethylformamide. The technology of liquid transfer from the window 4 into the compartment 2 secures a simultaneous start of condensation reactions in all parts of the carrier. If it is not necessary to comply with this supposition, it is possible to apply the solution of the activated component, as well as solutions used for washing and cleavage of protective groups by means of micropipettes driven by means of a stepping motor. The porosity of individual compartments 2 secures a uniform spreading of applied liquid. After having inserted a solution of the activated component, e.g. symmetrical anhydride amino of protected amino acid, of respective active ester, eventually of a mixture of the protected amino acid and activating agent, advantageously comprising an agent monitoring the condensation course, e.g. bromophenol blue, then a connection of another amino acid into a peptidic chain takes place. The concentration of an active component must be such that it may be included in the carrier in a sufficient surplus over the amount of free amino group present. Due to the relative high absorption capacity of cotton (1.0 g of DMF for 1 g of cotton) and relative low substitution applied for the synthesis (0.1 mol/g) of concentration 0.5 mol/l of activated component, a sufficient surplus is supplied for securing a quick course of the reaction. After the reaction has been finished, i.e. after the blue coloring of the carrier has disappeared in case of monitoring with bromophenol blue, liquid is removed from the carrier by passing the carrier together with a porous dry material 6, between rollers 5.

Figure 2:
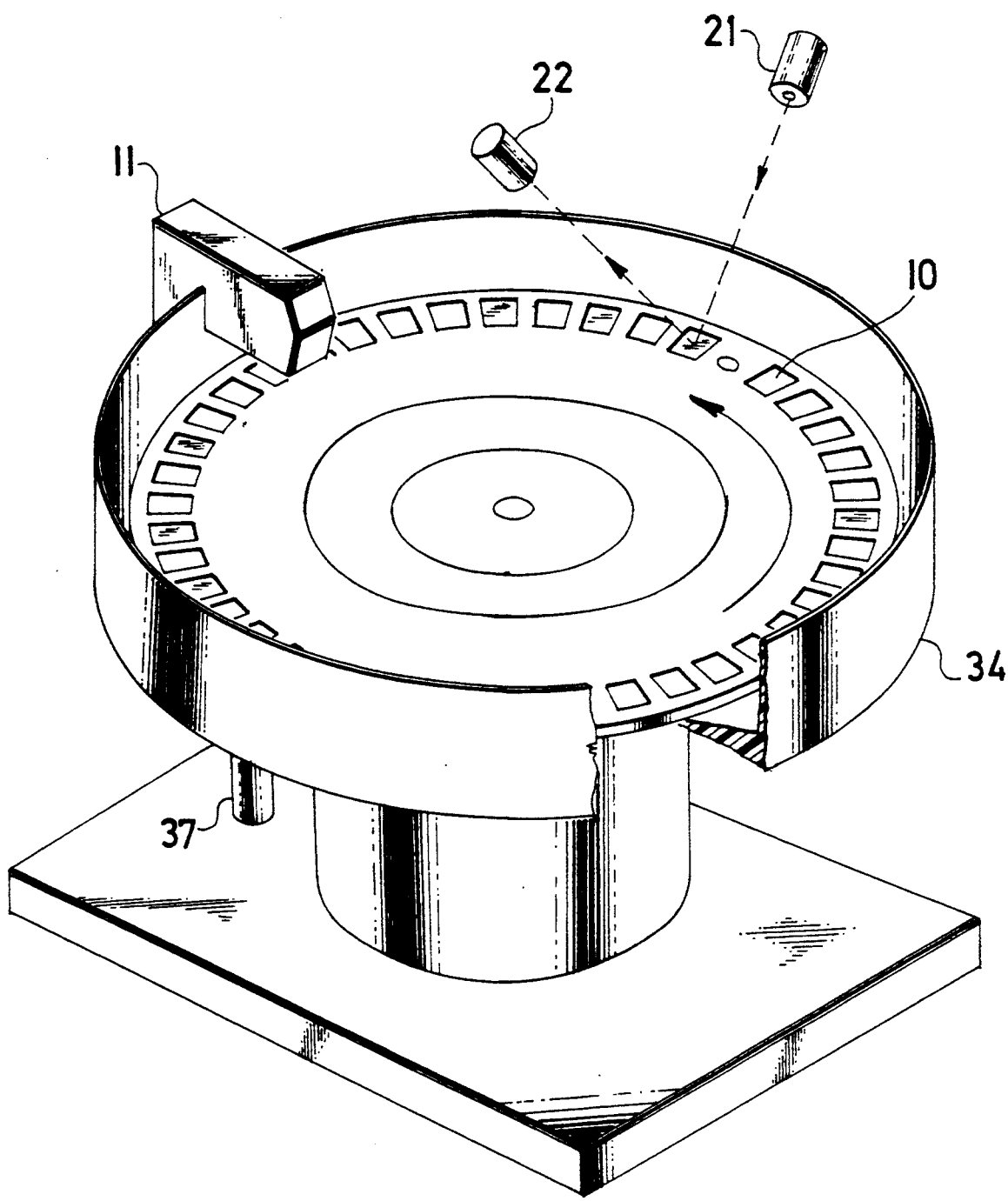
FIG. 2 is an enlarged schematic perspective view of another embodiment of the apparatus.

The rotary apparatus according to FIG. 2 and FIG. 3 is formed by a disk made of inert material provided on its circumference with compartments 10. Over the disk, at the spot at which individual compartments 10 enter, a dosing head 11 is situated. Over the level of the disk there is also situated an optical device consisting of a source 21 of a light radiation and detector 27 of the reflected radiation. The disk is seated on the same axle as a driving motor 12 and rotary incremental position pick-up 13. The disk 8 is situated in a tank 34 provided with an exhaust device 35 having a separator 36, and a waste piping 37 which is led out into a waste vessel 38. The dosing head 11 comprises outlets 14 for activated components (one being shown) and outlets 15 for washing solutions and solutions used for removing the protecting groups. Outlets 14 are connected by means of piping to reservoirs 17 of activated components situated in cooled boxes 19, the temperature of which is controlled by a controller 20. The outlets 15 are connected to reservoirs 18 of washing solutions and solutions used for removing the protecting groups.

The dosing system is formed by a container 23 of compressed inert gas, first and second pressure reducing valves 24, 25, first and second pressure reducing valves 24, 25, first and second two-way valves 28, 29, first and second three-way valves 26, 27, a measuring loop 30 of activated components consisting of a transparent hose and a sensor 32 of the activated component and a measuring loop 31 of washing solutions and solutions applied for removing the protecting groups together with a sensor 33 of this solution. All controlled elements, such as the motor 12, valves and the like, or pick-up elements are connected to a control computer 16.

The number of outlets 14, 15 of the dosing head 11 results from the number of activated components applied for the synthesis of peptides and from the number of washing solutions determined for removing the protecting groups. The dosing and transport of activated components and solutions is carried out by means of pressure of inert gas. The process uses two pressure levels controlled with pressure reducing valves 24, 25. The first pressure reducing valve 24 controls pressure needed for transporting the measured quantity of liquids into the dosing head 11 and from it to the respective compartment 10. The second pressure valve 25 determines optimum velocity of transfer of the measured liquid in measuring loops 30, 31. The application of activated components and solutions may be carried out also with a higher number of dosing heads 11, situated over individual compartments 10 along the circumference of the disk. After having supplied the memory for the computer with parameters of the process from which the most important is the number and sequence of bonded activated components, the synthesis may be started.

The motor 12 turns the disk in such a way that successively into each compartment 10 with a functionalized carrier there may be sprayed, from the reservoir 17, by means of the dosing device, the respective activated components. The measuring of the dose of the activated component is carried out in such way that after having stabilized the position of the respective compartment 10 under the dosing head 11, then the activated component, after the liquid path has been opened between the reservoir 17 and the first measuring loop 30 by means of the three-way valve 26, is pressed out, due to pressure of the inert gas, through the transparent pipe for such a long time until the sensor 32 of the activated component presence is put into function. At this moment the first three-way valve 26 is changed over in such a way that it interconnects the dosing loop 30 and the pressure gas inlet, and, after a needed delay, the first two-way valve 28 is opened, which, by means of inert gas pressure set up with the pressure reducing valve 24, pulls out the measured quantity of the activated component via the respective outlet 14 of the dosing head 11 from the measuring loop 30 onto the carrier. By a successive turning of the disk under the dosing head 11, all needed hydraulic paths are activated in this way from reservoirs 17 of activated components untill all compartments 10 of the disk are attended. The motor 12 goes on turning the disk slowly, and one watches, by means of the optic device consisting of the source 21 and detector 22 of the light radiation, the course of the chemical reaction, in this case condensation, in individual compartments. This is done by comparing the color of active compartments 10 with that of a reference compartment. For watching the course of the reaction with the optical device, the solution of the activated component must be completed with a respective agent, e.g. bromophenol blue. At the moment when it is found out by means of the optical device that in all active compartments 10 the reaction proceeded well, the disk 8 is rotated to such revolutions that residuals of unbonded active components may be centrifuged away. The centrifuging having been finished, the disk 8 is turned slowly again. Washing solution then is measured out by means of the hydraulic path through valves 25 and 27, measuring loop 31 and sensor 33. The defined quantity of washing solution is then sprayed through outlets 15 by means of valves 24, 29, and 27, onto all compartments 10 in an analogous way as described above for dosing the active components. After again centrifuging, this step may be repeated several times. Then, in the same way, the application of the solution used for removing the protecting groups, as well as the repeated centrifuging, take place. After several such steps, when the washing solution is applied and then centrifuged, the synthesis may go to the next step in which the further component is bonded in the described way. The sequence of bonded activated components in individual compartments 10 of the disk is determined in this way on the basis of the peptide sequence determined by the computer, and the synthesis velocity depends on the slowest condensation from all simultaneously proceeding condensations.

The interval for bonding individual activated components is limited and if e.g. in some compartment the bonding was not successful, the application of the same component is repeated in the next cycle, eventually the synthesis of this peptide does not continue in following cycles.

Examples of syntheses which do not limit the mentioned technology but only illustrate it follow.

In Example 1 set forth in Czechoslovakian Patent Application No. PV 1280-89, and in corresponding European Patent Publication No. 385,433 published Sep. 5, 1990, a cotton band (width 3 cm, length 280 cm, weight 23.1 mg/cm) was shaken with a mixture of trifluoroacetic acid (25 ml) and dichloromethane (75 ml) for 15 minutes, washed successively with dichloromethane (3×100 ml), 10% solution of diisopropylethylamine in dichloromethane (2×100 ml) and dichloromethane (3×100 ml) and dried in vacuo. The band was then shaken with a mixture of tertbutyloxycarbonylglycine (4.4 g), dicyclohexylcarbodiimide (5.15 g), dimethylaminopyridine (3.05 g) and dimethylformamide (100 ml) for 4 hours at room temperature. After washing with dimethylformamide (3×100 ml), ethanol (3×100 ml. and dichloromethane (3×100 ml) and drying, the capacity of the carrier was 3.1 $\mu$mol/cm$^2$.

EXAMPLE 1

Using methodology similar to that of Example 1 set forth in Czechoslovakian Patent Application No. PV 1280-89, a cotton strip (width 3 cm, length 27 cm) was esterified with Fmoc-Gly. After this there was added to the Fmoc-Gly the arm HO—CH$_2$C$_6$CH$_4$O(CH$_2$)$_3$COOH. The carrier modified in this way was separated into nine parts and three of them were situated on a glass pad. Into each of these parts of the carrier, there were added 200 $\mu$l of a solution comprising Fmoc-Met (F-moc-Leu, F-moc-Nle), diisopropylcarbodiimide, hydroxybenzotriazole (all 0.5M) and dimethylaminopyridine (0.15M). This was carried out in such a way that solutions were laid into a square of glass fiber (3×3 cms) which was then pressed onto the cotton carrier and in this way the transfer of the liquid into the carrier was realized. After twelve hours, the treated parts of the carrier were washed with dimethyl formamide and dichloromethane. The following solutions were added in a stepwise way using the above mentioned technique into the above mentioned parts in the quantity of 200 $\mu$l in the sequence:

1. dimethylformamide (3×1 min)
2. 20% of piperidine in dimethylformamide (1×2 min and 1×10 min)
3. dimethylformamide (5×1 min)
4. Solution of Fmoc-amino acid, N-hydroxybenzotriazole and diisopropylcarbodiimide (all 0,5M in dimethlyformamide) and bromophenol blue (0,5 mM in dimethylformamide)
5. dimethylformamide (3×1 min)

After the mentioned time of action, solutions were removed by pressing the carrier together with filtering paper and another portion of the solution was laid on. After the laying on of the solution 4, the carriers were getting blue, and the other step was carried out after the carrier had been discolored. In individual parts of the carrier there were connected in a stepwise way the following derivatives: Fmoc-Phe, Fmos-Gly-Gly and Fmoc-Tyr(But). In this way three various peptidic sequences were obtained at the same time (Tyr-Gly-Gly-Phe-Met (SEQ ID NO:1), Tyr-Gly-Gly-Phe-Leu (SEQ ID NO:2), Tyr-Gly-Gly-Phe-Nle (SEQ ID NO:3)). These peptides, after having been cleaved from the carrier (90% trifluoroacetic acid, 5% dimethylsulfide, 5% thioanisole, 3 hours at room temperature), were purified by means of HPLC and characterized in a standard way.

EXAMPLE 2

A strip of polypropylene modified with a hydroxypropyl group (Milligen Bioresearch, USA) was esterified in the same way as a cotton tissue, and a carrier was obtained of a substitution 0.1 mmol/g (determination by means of a cleavage of Fmoc group). Then the synthesis was carried out in the same way as in Example 1, only with the distinction that one put on less solutions (60 $\mu$l with respect to the lower specific weight of this carrier. The same peptides as in Example 1 were prepared on this carrier.

EXAMPLE 3

The synthesis of the above mentioned analogs of enkephalin was carried out on a cotton carrier as it was mentioned in Example 1, only with the distinction that all solutions were laid onto the carrier by means of a micropipette. The quality of obtained products was identical with the peptide quality yielded in Example 1.

EXAMPLE 4

The synthesis of the above mentioned analogs of enkephalin was carried out on a cotton carrier as it was mentioned in Example 1, only with the distinction that the compartmentized carrier was connected onto the disk circumference and all solutions were removed from the carrier by centrifuging. The quality of obtained products was identical with the quality of peptides yielded in Example 1.

EXAMPLE 5

Six square pieces of cotton (3×3 cm, modified by Fmoc-Gly substitution of 0.09 mmol/g) were placed on the perimeter of a planar rotor (diameter 25 cm) with six shallow compartments (3.2×4.5×0.2 cm.) To the center of the cotton piece the solutions in the order given at the particular example were added. After the given time the rotor was spun for 30 seconds at 2500 r.p.m. and next solution was added.

Typical synthetic protocol for the attachment of one amino acid residue consists of the following steps:
Cleavage:
S. 1) Addition of 20% piperidine in dimethylformamide (0.2 ml)
S. 2) Waiting 10 min.
S. 3) Spinning
Washing:
W. 1) addition of dimethylforamide (0.4 ml)
W. 2) Waiting 1 min.
W. 3) Spinning
Coupling:
C. 1) Addition of 0.1% solution of bromophenol blue in dimethylformamide spiked with N-hydroxybenzotriazole (80 μl)
C. 2) Spinning
C. 3) Addition of the solution of activated protected amino acid (0.4 ml)
C. 4) Waiting until the blue color of the dot formed in step C.1 disappears (5–120 min.)
C. 5) Spinning

EXAMPLE 6

Synthesis of Acyl Carrier Protein 65-74

In the first step of the synthesis performed according to Example 5, Fmoc-Gly-OCH$_2$C$_6$H$_4$OCH$_2$CH$_2$CH$_2$COOH was coupled to the cotton pieces in all six compartments. In the next steps the following amino acid derivatives were coupled to the modified carrier: Fmoc-Asn-OH, Fmoc-Ile-OH, Fmoc-Tyr(Bu$^t$)-OH, Fmoc-Asp(OBut)-OH, Fmoc-Ile-OH, Fmoc-Ala-OH, Fmoc-Ala-OH Fmoc-Glu(OB )-OH, Fmoc-Val-OH.

The protected amino acid (0.08 mmol) was dissolved in dimethylformamide (0.4 ml) together with N-hydroxybenzotriazole (0.08 mmol) and diisopropylcarbodiimide (0.08 mmol) was added. After 2 minutes the solution was added to the carrier. In the synthesis the following protocol was used.
Cleavage
Washing (3 x)
Coupling
Washing (3 x)

In the step S1 (see Example 5) of cleavage various concentrations of piperidine and cleavage times in particular cotton pieces were used.

Compartment 1–20% piperidine, 5 min.
2–20% piperidine, 10 min.
3–20% piperidine, 20 min.
4–50% piperidine, 2 min.
5–50% piperidine, 5 min.
6–50% piperidine, 10 min.

(Cleavage was started at different times so that it could be terminated in all compartments simultaneously by spinning.) At the end of the synthesis the compartments were washed by ethanol and dried. The peptides were cleaved by 50% trifluoroacetic acid, 2% anisole (1 h at room temperature), solution was evaporated in vacuo, dissolved in 3M acetic acid and lyophilized. The crude material was analyzed by HPLC (Vydac C18, 25×0.4 cm, gradient 20–100% methanol in 0.05% trifluoroacetic acid in 40 min.). The quality of peptides synthesized in compartments 4–6 were slightly worse than that from compartments 1–3. The optimal result was obtained from compartment 1. The product was characterized by amino acid analysis (Asp 2.05, Glu 1.04, Gly 1.14, Ala 2.03, Val 0.91, Ile 1.97, Tyr 0.85) and FAB Mass spectroscopy (M+H=1064; theory 1064).

EXAMPLE 7

Synthesis of [Ser$^{5,15}$]MCH

In the first step of the synthesis performed according to Example 5, N-Fmoc-4-methoxy-4'-(3-carboxypropyloxy)-benzhydrylamine was coupled to the cotton pieces in all six compartments. In the next steps the following amino acid derivatives were coupled to the modified carrier:

Fmoc-Asp(OBu$^t$)-OH, Fmoc-Thr(Bu$^t$)-OH, Fmoc-Met-OH, Fmoc-Arg(Mtr)-OH, Fmoc-Ser-(Bu$^t$)-OH, Fmoc-Met-OH, Fmoc-Val-OH, Fmoc-Gly-OH, Fmoc-Arg(Mtr)-OH, Fmoc-Val-OH, Fmoc-Tyr(Bu$^t$)-OH, Fmoc-Arg(Mtr)-OH, Fmoc-Pro-OH, Fmoc-Ser(But)-OH, Fmoc-Trp-OH, Fmoc-Glu(OBut)-OH, Fmoc-Val-OH.

The synthesis was performed in the same way as in Example 6 with the exception of the step S1 where the different bases were used for the cleavage of the Fmoc protecting group.

Compartment 1 - 20% piperidine, 10 min.
2 - 2M 4-benzylpiperidine, 10 min.
3 - 0.05M 4-piperidinopiperidine, 10 min.
4 - 0.5M 4-(aminomethyl)piperdine, 10 min.
5 - 0.5M tris(2-aminoethyl)amine, 10 min.
6 - 1M 1-(2-aminoethyl)piperazine, 10 min.

The finished peptides were cleaved and analyzed in the same manner as in Example 6. The peptide from compartment 1 and 2 were indistinguishable, other bases afforded the product of the inferior quality. Amino acid analysis: Asp 1.09, Thr 1.00, Ser 1.94, Glu 1.10, Pro 1.06, Val 3.25, Met 1.78, Tyr 0.91, Arg 2.85. FAB mass spectrum: 2069.

EXAMPLE 8

Synthesis of Acyl Carrier Protein 65-74

The synthesis was performed in the same way as in Example 6. The base used for the cleavage was 20% piperidine in dimethylformamide. In particular cotton pieces, the different protocol (number of washing) was applied.

| Compartment | |
|---|---|
| 1 - | Cleavage, Washing (1 x), Coupling, Washing (1 x) |
| 2 - | Cleavage, Washing (2 x), Coupling, Washing (2 x) |
| 3 - | Cleavage, Washing (4 x), Coupling, Washing (4 x) |
| 4 - | The same protocol as in the compartment 3, but the modification of the cotton was performed by periodate oxidation and hexamethylenediamine treatment |
| 5 - | Cleavage, Washing (1 x), Coupling, Washing (1 x) |
| 6 - | Cleavage, Washing (4 x), Coupling, Washing (4 x) |

In compartments 5 and 6, the solution of protected amino acid (0.08 mmol) and HOBt (0.08 mmol) in 0.2 ml dimethylformamide was added to the carrier separately from the 0.4M solution of diisopropylcarbodiimide in dimethylformamide (0.2 ml).

After the cleavage and analysis performed in the same way as in Example 6, all peptides were found indistinguishable.

EXAMPLE 9

Synthesis of Model Peptides

In the first step of the synthesis acid-labile amide linker (N-Fmoc-4-methoxy-4'-(3-carboxypropyloxy)-benzhydrylamine) was coupled to the cotton squares in compartments 1 to 5. The synthesis was performed in the same manner as in the Example 6, but the different sequence was assembled in all compartments.

| Compartment | |
|---|---|
| 1: | Ala—Val—Leu—Gly—His—Asp—Glu—Ala—Ala—Tyr—Ser—Lys—Asn—Arg—Arg—Ala—Val (SEQ ID NO: 4) |
| 2: | Asp—Thr—Met—Arg—Ser—Met—Val—Gly—Arg—Val—Tyr—Arg—Pro—Ser—Trp—Glu—Val (SEQ ID NO: 5) |
| 3: | Tyr—Ala—Ala—Ala—Ala—Ala—Ala—Ala—Ala—Ala—Ala—Ala—Ala—Ala—Ala—Ala—Ala—Ala—Ala—Ala—Ala—Val (SEQ ID NO: 6) |
| 4: | Tyr—Ala—Ala—Ala—Ala—Ala—Ala—Ala—Ala—Ala—D—Ala—Ala—Ala—Ala—Ala—Ala—Ala—Ala—Ala—Ala—Val |
| 5: | Tyr—Ala—Ala—Ala—Ala—Ala—Ala—D—Ala—Ala—Ala—Ala—Ala—Ala—Ala—D—Ala—Ala—Ala—Ala—Ala—Ala—Ala—Val |
| 6: | Ala—Ala—Ala—Ala—Ala—Ala—Ala—Ala—Ala—Ala—Val—Gly (SEQ ID NO: 7) |

Peptides from the cotton carrier in compartments 1 to 5 were cleaved by trifluoroacetic acid—phenol—water—thioanisole—ethanedithiol (82.5:5:5:5:2.5) mixture (1 h, r.t.) and worked up and characterized in the way described in Example 6. Cotton from compartment 6 was treated with 1M NaOH for 1 h, washed and extracted by trifluoroacetic acid. This extract was worked up in the usual way. All products were found more than 80% pure by HPLC. They had correct amino acid analysis and FAB mass spectrum.

EXAMPLE 10

Polystyrene resin (153 mg, 1% divinylbemzene, 300–400 mesh) was placed in the "tea bag" according to EP 0196174 (Houghten R. A.) and dimethylformamide was soaked into it. The cotton piece 3×3 cm (160 mg) was soaked by dimethylformamide too. The content of solvent in the carrier was determined by weighing. Both carriers were centrifuged (2000 r.p.m., 2 min.) and the content of solvent was determined again. Results of the experiment, together with the attempt to eliminate the liquid from the cotton by its compression together with the dry filtration paper are given in table 1.

TABLE 1

Solvent content in carriers after different treatment

| Material | Dry weight (mg) | DMF content after | | | | | |
|---|---|---|---|---|---|---|---|
| | | Soaking | | Compression | | Centrifugation | |
| | | mg | % | mg | % | mg | % |
| Cotton | 160 | 182 | 114 | 38 | 24 | 10 | 6.2 |
| Polystyrene | 153 | 268 | 175 | * | | 101 | 66 |

*Not determined

---

We claim:

1. A method of synthesizing peptides, comprising the steps of:
providing a planar carrier on a disk, which carrier is divided into a plurality of individual compartments, each compartment containing an inert porous material, a circular path being defined around said disk, said compartments being circumferentially spaced around said circular path, a functional group of an amino acid residue being anchored onto the inert porous material of each compartment to form a plurality of individual functionalized compartments;
arranging a dosing head at a fixed location adjacent said circular path, the dosing head including means for directly dispensing measured quantities of at least one liquid component from a common reservoir of such component;
positioning the disk so that a first one of the individual functionalized compartments is positioned to receive a liquid component directly dispensed by the dosing head;
directly dispensing a measured quantity of the liquid component to said first individual functionalized compartment from the common reservoir thereof, via the dosing head, the liquid component dispensed thereto providing an amino acid to form a covalent bond with the functional group of the amino acid residue in said first individual functionalized compartment positioned to receive the liquid component for peptide synthesis in said first individual functionalized compartment receiving the measured quantity;
rotating the disk to position a second individual functionalized compartment along the circular path to receive the liquid component dispensed by the dosing head; and
subsequently dispensing at least one other amino acid to another individual functionalized compartment in at least one other step for completing the synthesis of peptides.

2. The method of claim 1 wherein the functional group of at least one of the individual functionalized compartments is provided by an amino acid of a peptide.

3. A method of synthesizing peptides, comprising the steps of:
providing a solid planar carrier divided into a plurality of individual compartments, each compartment containing an inert porous material, a path being defined on said carrier, said compartments being spaced along said path, a functional group of an amino acid residue being anchored onto the inert porous material of each compartment to form a plurality of individual functionalized compartments;
arranging a dosing head at a fixed location adjacent said path, the dosing head including means for directly dispensed measured quantities of at least one liquid compartment from a common reservoir of such component;
positioning the carrier so that a first one of the individual functionalized compartments is positioned to receive a liquid component directly dispensed by the dosing head;
directly dispensing a measured quantity of the liquid component to said first individual functionalized compartment from the common reservoir thereof, via the dosing head, the liquid component dispensed thereto providing an amino acid to form a covalent bond with the functional group of the amino acid residue in said first individual functionalized compartment positioned to receive the liquid component for peptide synthesis in said first individual functionalized compartment receiving the measured quantity;
moving the carrier to position a second individual compartment along the path to receive the liquid component applied by the dosing head; and
subsequently dispensing at least one additional measured quantity of one of said liquid component providing an amino acid to another individual functionalized compartment in at least one other step for peptide synthesis.

4. The method of claim 3 wherein the functional group of at least one of the individual functionalized compartments is provided by an amino acid of a peptide.

5. A method of synthesizing peptides, comprising the steps of:
providing a planar carrier on a disk, which carrier is divided into a plurality of individual compartments, each compartment containing an inert porous material, a circular path being defined around said disk, said compartments being circumferentially spaced around said circular path, a functional group of an amino acid residue being anchored onto the inert porous material of each compartment to form a plurality of individual functionalized compartments;
arranging a dosing head at a fixed location adjacent said circular path, the dosing head including means for directly dispensing measured quantities of at least one liquid component from a common reservoir of such component;

positioning the disk so that a first one of the individual functionalized compartments is positioned to receive a liquid component directly dispensed by the dosing head;

directly dispensing a measured quantity of the liquid component to said first individual functionalized compartment from the common reservoir thereof, via the dosing head, the liquid component dispensed thereto providing an amino acid to form a covalent bond with the functional group of the amino acid residue in said first individual functionalized compartment positioned to receive the liquid component for peptide synthesis in said first individual functionalized compartment receiving the measured quantity;

rotating the disk to position a second individual functionalized compartment along the circular path to receive the liquid component dispensed by the dosing head; and subsequently dispensing at least one additional measured quantity of one of said liquid component providing amino acid to another individual functionalized compartment in at least one other step for peptide synthesis.

6. A method of synthesizing peptides, comprising the steps of:

providing a solid planar carrier divided into a plurality of individual compartments, each compartment containing an inert porous material, a path being defined on said carrier, said compartments being spaced along said path;

anchoring at least one functional group of an amino acid residue onto the inert porous material of each compartment to form a plurality of individual functionalized compartments;

arranging a dosing head at a fixed location adjacent said circular path, the dosing head including means for directly dispensing measured quantities of at least one liquid component from a common reservoir of such component;

positioning the carrier so that a first one of the individual functionalized compartments is positioned to receive a liquid component directly dispensed by the dosing head;

directly dispensing a measured quantity of the liquid component to said first individual functionalized compartment from the common reservoir thereof, via the dosing head, the liquid component dispensed thereto providing an amino acid to form a covalent bond with the functional group of the amino acid residue in said first individual functionalized compartment positioned to receive the liquid component for beginning the synthesis of a peptide from the functional group of said first individual functionalized compartment receiving the measured quantity;

moving the carrier to position a second individual functionalized compartment along the path to receive the liquid component dispensed by the dosing head; and subsequently dispensing at least one additional measured quantity of one of said liquid component providing an amino acid to another individual functionalized compartment in at least one other step for completing the synthesis of peptides.

* * * * *

UNITED STATES PATENT AND TRADEMARK OFFICE
CERTIFICATE OF CORRECTION

PATENT NO. : 5,338,831
DATED : August 16, 1994
INVENTOR(S) : Lebl et al.

It is certified that error appears in the above-identified patent and that said Letters Patent is hereby corrected as shown below:

Title page, item [56] References Cited, the date "9/1973" for

Won Kil Park et al. should be --9/1971--.

Column 1, line 20, "yon" should be --von--.

Column 1, line 50, and Column 2, line 14, "Bartcling" should be --Barteling-- in both instances.

Column 14, line 22, "dispensed" should be --dispensing--.

Signed and Sealed this

Eighth Day of November, 1994

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

Tyr  Gly  Gly  Phe  Met
   1                         5

( 2 ) INFORMATION FOR SEQ ID NO:2:

( i ) SEQUENCE CHARACTERISTICS:
      ( A ) LENGTH: 5 amino acids
      ( B ) TYPE: amino acid (D) TOPOLOGY: linear (ii) MOLECULE TYPE: peptide (xi) SEQUENCE DESCRIPTION: SEQ ID NO:2:

```
Tyr Gly Gly Phe Leu
1               5
```

(2) INFORMATION FOR SEQ ID NO:3:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 5
(D) OTHER INFORMATION: /label=Xaa
/ note="Xaa=Nle."

(xi) SEQUENCE DESCRIPTION: SEQ ID NO:3:

```
Tyr Gly Gly Phe Xaa
1               5
```

(2) INFORMATION FOR SEQ ID NO:4:

(i) SEQUENCE CHARACTERISTICS:
(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO:4:

```
Ala Val Leu Gly His Asp Glu Ala Ala Tyr Ser Lys Asn Arg Arg Ala
1               5                   10                  15
Val
```

(2) INFORMATION FOR SEQ ID NO:5:

(i) SEQUENCE CHARACTERISTICS:
(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO:5:

```
Asp Thr Met Arg Ser Met Val Gly Arg Val Tyr Arg Pro Ser Trp Glu
1               5                   10                  15
Val
```

(2) INFORMATION FOR SEQ ID NO:6:

(i) SEQUENCE CHARACTERISTICS:
(A) LENGTH: 22 amino acids
(B) TYPE: amino acid
(D) TOPOLOGY: linear (ii) MOLECULE TYPE: peptide (xi) SEQUENCE DESCRIPTION: SEQ ID NO:6:

```
Tyr Ala Ala Ala Ala Ala Ala Ala Ala Ala Ala Ala Ala Ala Ala Ala
1               5                   10                  15
Ala Ala Ala Ala Ala Val
                20
```

-continued (2) INFORMATION FOR SEQ ID NO:7:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:7:

```
Ala Ala Ala Ala Ala Ala Ala Ala Ala Ala Val Gly
 1               5                  10
```